(12) United States Patent
Bergt et al.

(10) Patent No.: US 8,585,686 B2
(45) Date of Patent: Nov. 19, 2013

(54) FEMTOSECOND LASER SYSTEM FOR THE EXACT MANIPULATION OF MATERIAL AND TISSUES (75) Inventors: Michael Bergt, Jena (DE); Manfred Dick, Gefell (DE)

(73) Assignee: Carl Zeiss Meditec AG, Jena (DE)

( * ) Notice: Subject to any disclaimer, the term of this patent is extended or adjusted under 35 U.S.C. 154(b) by 1861 days.

(21) Appl. No.: 10/501,679

(22) PCT Filed: Jan. 17, 2003

(86) PCT No.: PCT/EP03/00446
§ 371 (c)(1),
(2), (4) Date: Dec. 17, 2004

(87) PCT Pub. No.: WO03/059563
PCT Pub. Date: Jul. 24, 2003

(65) Prior Publication Data
US 2005/0107773 A1 May 19, 2005

(30) Foreign Application Priority Data
Jan. 18, 2002 (DE) .................. 102 02 036

(51) Int. Cl.
*A61B 18/20* (2006.01)

(52) U.S. Cl.
USPC .............. 606/4; 606/3; 606/10; 128/898

(58) Field of Classification Search
USPC .......... 606/4–6, 10–13; 128/898; 607/88, 89; 372/39, 43.01, 96, 72, 75; 359/333, 359/340, 341.3, 342–349
See application file for complete search history.

(56) References Cited

U.S. PATENT DOCUMENTS

| | | | |
|---|---|---|---|
| 4,646,308 A | 2/1987 | Kafka et al. | 372/25 |
| 4,864,577 A | 9/1989 | Aoshima et al. | |
| 4,901,718 A | 2/1990 | Bille et al. | |
| 4,907,586 A | 3/1990 | Bille et al. | |
| 4,941,093 A | 7/1990 | Marshall et al. | |
| 5,336,215 A | 8/1994 | Hsueh et al. | |
| 5,520,679 A | 5/1996 | Lin | 606/5 |
| 5,656,186 A | 8/1997 | Mourou et al. | 219/121.69 |
| 5,870,421 A | 2/1999 | Dahm | 372/75 |
| 5,984,916 A | 11/1999 | Lai | |
| 6,016,324 A * | 1/2000 | Rieger et al. | 372/25 |
| 6,146,375 A * | 11/2000 | Juhasz et al. | 606/6 |

(Continued)

FOREIGN PATENT DOCUMENTS

| | | |
|---|---|---|
| DE | 197 27 573 | 5/1998 |
| DE | 197 46 483 | 5/1999 |

(Continued)

OTHER PUBLICATIONS

Cha et al., Incorporation of a cavity-dumped oscillator in a longwavelength injected femtosecond terawatt Ti:sapphire laser, Nov. 2000, Optics Communications, 185, 413-418.*

(Continued)

*Primary Examiner* — Ahmed Farah
(74) *Attorney, Agent, or Firm* — Leydig, Voit & Mayer, Ltd.

(57) ABSTRACT

A a device for the exact manipulation of material, especially of organic material. includes a pulsed laser system with a radiation source, said radiation source being a cavity-dumped fs oscillator.

19 Claims, 2 Drawing Sheets

(56) References Cited

U.S. PATENT DOCUMENTS

| | | | |
|---|---|---|---|
| 6,254,595 B1 | 7/2001 | Juhasz et al. | |
| 6,290,695 B1 | 9/2001 | Kuhnert et al. | 606/5 |
| 6,325,792 B1 | 12/2001 | Swinger et al. | |
| 6,333,485 B1 * | 12/2001 | Haight et al. | 219/121.68 |
| 6,363,090 B1 | 3/2002 | Wintner et al. | 372/21 |
| 6,394,164 B1 | 5/2002 | Lafond | |
| 6,573,026 B1 * | 6/2003 | Aitken et al. | 430/290 |
| 6,603,600 B2 * | 8/2003 | Pang | 359/348 |
| 6,623,476 B2 | 9/2003 | Juhasz et al. | |
| 7,128,737 B1 | 10/2006 | Goder et al. | |
| 2003/0099452 A1 * | 5/2003 | Borrelli et al. | 385/129 |
| 2004/0111083 A1 * | 6/2004 | Gross et al. | 606/5 |

FOREIGN PATENT DOCUMENTS

| | | |
|---|---|---|
| DE | 19746483 | 5/1999 |
| DE | 199 07 722 | 8/1999 |
| JP | 63306681 A | 12/1988 |
| JP | 5102618 A | 4/1993 |
| JP | 6-181944 A | 7/1994 |
| JP | 6-277248 A | 10/1994 |
| JP | 11267861 | 10/1999 |
| JP | 2001-212685 A | 8/2001 |
| JP | 2001-232487 A | 8/2001 |
| JP | 2001-239379 A | 9/2001 |

OTHER PUBLICATIONS

K. Koenig et al. "Nanodissection of human chromosomes with near-infrared femtosecond laser pulses", Optical Society of America, Optics Letters, vol. 26, No. 11, Jun. 1, 2001, pp. 819-821.

Yong Ho Cha et al., "Incorporation of a cavity-dumped oscillator in a long-wavelength injected femtosecond terawatt Ti:sapphire laser", Optics Communications 185, 2000, pp. 413-418.

Shinjin Notification from Japanese Application No. 2003-559712 dated Dec. 24, 2010.

* cited by examiner fig 1 fig 2 fig. 3 fig 4 fig 5

FEMTOSECOND LASER SYSTEM FOR THE EXACT MANIPULATION OF MATERIAL AND TISSUES

The invention relates to a femtosecond laser system for the precise machining of material and tissue, in particular a laser apparatus for the precise, micrometer-accurate machining of organic material, preferably an eye.

BACKGROUND

In a valuable contribution to the state of the art it is described in the applicant's patent specification DE 197 46 483 how macroscopic quantities of material are ablated, evaporated or melted with micrometer precision in the machining of extensive areas of materials with lasers with a large spot diameter (mm-cm) ($CO_2$ lasers, Nd:YAG, excimers, etc.).

In a further valuable contribution to the state of the art, there is described in the applicant's patent specification DE 197 27 573 an algorithm as to how a laser beam can be deflected to ensure the best possible and precise machining of material.

In U.S. Pat. No. 5,656,186, a method for machining material while simultaneously avoiding or minimizing harmful side effects (melt edges, thermal damage, acoustic shock waves, cracking) by choosing a special pulse duration depending on the material.

The material-machining effect of the laser is restricted to a small spatial area of the laser focus (typically some $\mu m^3$) in which the light intensity is high enough to exceed the threshold of the optical breakdown. Localized to this focus volume, the cohesion of the material is destroyed and a cavitation bubble forms. If the laser focus is guided to a new position for each laser pulse, linear, two-dimensional or three-dimensional cut patterns can be generated. At the end of the machining, the distance between adjacent cavitation bubbles must approximately correspond to the focus diameter so that the material can easily be mechanically detached along the cuts.

Existing laser apparatuses for machining material with femtosecond laser pulses use regenerative amplifiers with which individual pulses of a femtosecond oscillator are amplified. While the oscillator itself provides pulse energies in the nanojoule range only, the pulses can be amplified with a regenerative amplifier up to some millijoules of pulse energy. The repetition rates are limited to some 10 s of kHz by using Pockels cells for coupling and decoupling in the amplifier. While these laser sources are suitable for uses with high ablation rates per laser pulse, they are not ideal for the use described above for precision cuts.

In K. König et al., *Optics Letters Vol.* 26, No.11 (2001) it was described how cuts can also be made in tissue with nanojoule pulses from a femtosecond oscillator. However, as a single laser pulse does not lead to the formation of a cavitation bubble, but several pulses positioned at the same point are necessary to achieve a cutting action, this method is suitable only for very fine cut figures on a micrometer scale. This laser source is not suitable for industrial or medical use.

SUMMARY OF THE INVENTION

An object of the present invention is to provide a device for the precise machining of material with which these disadvantages of the state of the art are overcome.

The present invention provides a device for the precise machining of material, in particular organic material, comprising a pulsed laser system with a beam source, a cavity-dumped fs oscillator being provided as beam source.

The present invention provides a device for the precise machining of material, in particular organic material, comprising a pulsed laser system with a cavity-dumped fs oscillator as beam source in which a working beam of the beam source can be applied to the material using a beam apparatus with at least one means for beam deflection, the pulse emission correlating with the beam deflection and the means for beam deflection including means for releasing laser pulses. By release is meant that the laser is released for a laser pulse and the laser pulse is initiated as soon as the laser can again emit a laser pulse corresponding to its maximum repetition rate. By correlation of the pulse emission with the beam deflection is meant in particular that the pulse emission can take place when the beam has been steered to a specific point, the pulse emission is thus triggered depending on the beam deflection.

The present invention provides a device for the precise machining of material, in particular organic material, comprising a pulsed laser system with a cavity-dumped fs oscillator as beam source, the energy of the radiation being approximately 100 nJ to 10 µJ, preferably 500 nJ to 5 µJ. The repetition rate of the radiation is preferably 50 khz to 1 Mhz, particularly preferably 100 khz to 500 khz. The focus diameter of the radiation is preferably approximately 500 nm to 10 µm, particularly preferably 3 µm to 5 µm. The pulse duration of the radiation is preferably approximately 100 fs to 1 ps, particularly preferably 200 fs to 300 fs.

The means for beam formation and/or beam deflection or, in more general terms, the beam-formation and deflection systems, can include diffractive or refractive microlens systems or adaptive lens systems or standard optical systems. Several standard or conventional optical elements can be replaced by diffractive or refractive elements. When using such a relatively costly beam-formation and deflection system, relatively simple lasers can be used.

The named device for the precise machining of material is preferably used for ophthalmological eye treatment, in particular for the correction of the defective vision of an eye. The device can be used to cut a flap or lenticle in the cornea to correct the defective vision. In addition to cutting the lenticle, refractive structures, for example in the form of areally adjacent spots or a spot cloud, can be produced in the cornea with the device according to the invention.

Likewise, laser shots can be set directly to produce refractive structures. For example, small bubbles can be produced in the eye lens by evaporation of material or liquid. For this, very many laser shots of relatively low energy are necessary, as can be provided with the device according to the invention.

It is likewise possible with the device according to the invention to introduce targeted cuts into the tissue, for example the eye lens, and thus improve the curvability and elasticity of the eye lens, as the adjacent tissue parts can now more easily be pushed against one another. The device for the precise machining of material, in particular organic material, is used in this design of the invention as a device for treating presbyopia. Beam formation takes place either conventionally or with diffractive or refractive microlens systems or adaptive lens systems. The beam deflection preferably takes place via scan systems.

Directly diode-pumped femtosecond oscillators (optionally with a SESAM (semiconductor saturable absorber mirror)) for starting and stabilizing the mode locking and chirped mirrors for dispersion compensation in the resonator represent an ideal source. Through "cavity dumping", microjoule pulse energies can then be produced at a reduced repetition rate instead of the nanojoule pulses normally emitted with several tens of MHz. Instead of passively decoupling a small portion of the intracavity pulse energy (typically about one percent) during each rotation of a laser pulse in the resonator, the laser pulse is left complete in the resonator for several rotations and then there is a single active decoupling of a larger portion of the laser capacity from the resonator. The remaining laser pulse energy is then amplified again in several rotations in the resonator to a saturation value until a further pulse is decoupled. Given the same average laser capacity of some 100 s of mW, in this way laser pulses up to the microjoule range are thus produced at repetition rates of 0—some MHz. For active decoupling of the laser pulses, electrooptical or acoustooptical deflectors with rapid response times can be used. Pulse durations of less than 10 ps, preferably much shorter than 1 ps, preferably 100-200 fs are particularly preferably produced.

The material, preferably to be machined with micrometer precision, can include material with structures in the micrometer range, lattices, contact lenses, plastics, intraocular lenses (IOL), semiconductor wafers, microoptical elements etc. Organic material, such as for example tissue, particularly preferably the human eye, is particularly preferred.

The pulsed laser system is an arrangement of a laser beam source for the production of fs pulses and corresponding optical devices, in particular mirrors, lenses, etc.

Through this laser device, a system is provided the pulse energies of which make possible microscopic and macroscopic cut figures, preferably with micrometer accuracy, with a simultaneously high repetition rate. If—as in the state of the art—oscillators are post-amplified in regenerative amplifiers to produce microjoule pulse energies, the Pockels cells used for coupling and decoupling into the amplifier limit the repetition rate of the laser amplifier system. These disadvantages do not exist with the laser according to the invention. The device according to the invention is capable of generating microjoule pulse energies at adjustable repetition rates from zero up to some MHz. Pulse energies of a few microjoules and repetition rates of some 100 s of kHz are particularly preferably used. The oscillators then operate with average capacities of some 100 s of mW. A directly diode-pumped oscillator is particularly preferably used as beam source. This is particularly easy and reliable.

In one design of the device according to the invention, it is provided that the means for beam deflection are operated in scan mode. The working beam of the beam source can be deflected to paths periodically recurring in one dimension with the result that for example circular paths of different diameters or spiral paths can be produced. The paths of the working beam can be produced by a device held rotating or in another manner on a path, for example by a mirror, a lens, a lattice or similar. The means for beam deflection can include scanners, e.g., mechanical scanners, which are housed movable on preset paths. The present invention uses deflection systems that deflect the laser to the natural paths of the deflection system, e.g., to orbits in the case of rotating deflection systems. Instead of arriving at individual positions and initiating a laser pulse there, as soon as the preset position is reached and the deflection system is at rest again, the path of the deflection system is traveled without stops and the pulses are emitted beginning at a defined point in time at a preselected repetition rate preset via the path speed of the focus movement. Thus as soon as the focus position has reached a specific point, the laser is released or triggered, i.e. instructed to emit a laser pulse. By release is meant that the laser is released for a laser pulse and this laser pulse is initiated as soon as the laser can again emit a laser pulse corresponding to its maximum repetition rate. This leads to a trail of effective volumes, i.e. points in the material modified by the laser focus during the short pulse duration, along an essentially predefined path that is characterized in particular in that adjacent effective volumes are placed at constant, predefined intervals, for example of the order of the focus diameter. By slight modification of the natural path of the deflection system, e.g. by a slight reduction in the orbit radius, for example by the distance between adjacent effective volumes, further trails can be plotted which add up to form a cut surface. For example, concentric paths or spiral paths or similar can be produced here. If a deflection mirror is used, this can take place for example by changing the inclination while the rotation of the mirror remains constant. The aim is to cover the desired cut surface with a uniform grid of effective volumes or laser foci. The natural paths of the deflection system can be traveled very swiftly in a defined time sequence. The adjustment of the time sequence of the laser pulses then leads to the desired covering of the cut surface with laser shots.

Cavity-dumped fs oscillators have properties of the beam source required by this procedure, namely triggerability at the times preset by the deflection system. The individual pulses of the beam source are therefore initiated when the deflection system has reached the preset position. Advantageous are path movements in which pulses can be initiated at equal time intervals. In the case of the short pulse lengths, high maximum repetition rates and moderate pulse energies required here, cavity-dumped fs oscillators currently represent the ideal radiation sources for the system according to the invention.

In the case of a further embodiment of the present invention, beam apparatuses for beam formation and/or beam guidance and/or beam deflection and/or beam focusing are also provided. Through these beam apparatuses, the beam can thus be accurately steered and guided to the material to be machined, just as the planned use requires. The ultrashort laser pulses focused here on a focus diameter of the order of 1 μm can loosen the material cohesion in a small, precisely defined, focus volume, or cause structural changes in the material without thermally, acoustically or mechanically loading adjacent areas in the material. For macroscopic cuts and structures measured in centimeters, the laser focus is scanned in three dimensions through the material to be machined. The use determines how beam source, beam guidance and formation, scanner, scan algorithm and focusing lens system are matched in order to achieve a high machining speed with simultaneously high precision.

The beam formation preferably takes place by means of a telescope (preferably a Galilean telescope with converging and scatter lens) which expands the beam diameter such that the laser can be focused on a correspondingly small focus. A lens system which largely minimizes the imaging errors of the telescope is preferably used.

The beam guidance preferably takes place through mirrors or mirror pairs with which the beam can be aligned into the individual sub-components.

Conventional scanners or mechanical laser beam-deflection systems such as galvanometer mirrors in closed-loop operation, etc. can perform the beam deflection. However, mechanical scanners which travel preset paths (e.g. orbits) and as a result of which laser pulses are initiated by triggering the beam source at the positions provided are preferred. Thus a large area of the cut surface can be worked at full repetition rate with relatively slow scanner movements. If work is to be carried out in even smaller areas of the cut surface (e.g. if the orbit radius becomes too small), the repetition rate of the laser can preferably also be reduced. In a small area of the cut surface (if e.g. the orbit radius becomes very small), the repetition rate is then preferably matched to the then decreasing maximum path speed which is governed by the limited angular speed of the deflection mechanism, and reduced. With a deflection unit which is based on the rotation of an optical deflection element, it can be technically simpler to operate at a constant speed and thus a constant angular speed of the path movement of the laser focus. With each decreasing or increasing orbit, the repetition rate of the laser can then be adjusted to the new path speed resulting from the changed path radius. The machining of an area of a circle results in a machining period increased only by a factor of 2, than when all spots were set at maximum repetition rate. By adjusting the speed of the deflection unit in a few stages during machining, the machining period can be reduced still further.

The beam-focusing apparatus serves to destroy the cohesion of the material in the focus of the beam on or within the material (photodisruption). In general, this is accompanied by a local evaporation of the material. For this, the laser is preferably focused on a diameter in the micrometer range. This lies near to the diffraction limit of light in the visible or near infrared range. The focusing lens system therefore preferably has a high numerical aperture and thus a short focal length and a large optical opening (expanded laser beam diameter). The beam leaving the laser source is expanded in diameter before focusing on the material or tissue. The systems for beam guidance, deflection and focusing are therefore preferably designed for a large beam diameter.

Laser source, beam deflection (scanner) and focusing lens system are matched such that precise and swift cutting is made possible by way of photodisruption. Laser spots with a focus diameter of some 100 s of nm to some μm with a spot distance of the order of the spot diameter are placed in the material.

In a particularly preferred version, the beam apparatuses, in particular the deflection apparatuses, are programmable. As a result of the matchability of the individual beam apparatuses and the control by corresponding programmers, the system of beam apparatuses together with the pulsed laser system can be set precisely to the material and the cutting requirements for which it is to be used. Thus the set of parameters can be preselected and matched in relation to the transparence and refractive power of the material to be machined and also the requirements as regards cutting geometry and operation duration.

In a further preferred version of the present invention, holding devices are also provided for positioning and/or fixing the material to be machined. As a result of these holding devices it is ensured that the micrometer-accurate structures which can be produced by the laser according to the invention are not adversely affected by uncontrolled movements of the material to be machined, in particular the eye.

Such a fixing and positioning device can be a simple clamping device for a workpiece which is preferably equipped with multiaxial alignment capacities for moving and tilting of the workpiece for optimum alignment. Fixing apparatuses for medical applications on organs such as for example the eye must also be adapted to the biological conditions concerned. The human eye can be fixed for example with the help of a contact lens and a vacuum suction ring.

A positioning device can preferably be a contact lens. This contact lens can be either flat or preferably largely adapted to the curvature of the material to be machined, in particular the cornea.

A suction ring is preferably used as a fixing device. The suction ring is preferably attached securely to the beam hole of the laser apparatus, which leads to a defined position of the cornea relative to the laser focus.

In the case of a further device of the present invention, laser pulses of 100 nJ to 100 μJ, preferably 1 μJ of pulse energy are provided by the cavity-dumped fs oscillator. With this pulse energy, a photodisruption can be initiated in the micrometer range in the triggered area of the material and a cavitation bubble produced, in particular if the pulse duration is less than 300 fs. A shot set alongside will produce a further cavitation bubble adjacent to this cavitation bubble. As a result of these bubbles, the material structure is then destroyed permanently or for a period lasting until at least the end of machining.

Laser pulses with repetition rates of 10 kHz to 10 MHz are particularly preferably provided by the cavity-dumped fs oscillator. The repetition rate is preferably geared to the speed of a deflection system (e.g. maximum speed of the deflection lens system). For use on the eye, a 300 kHz repetition rate at approx. 50 Hz speed, which results in a machining time of less than a minute, is preferably used.

With these repetition rates, the laser action for the photodisruption can be precisely localized in tune with the preset pulse energy and the deflection apparatuses. The material structure is thereby destroyed in a sharply limited focus volume, while in general there is no change in the material in closely adjacent areas (less than a micrometer away). This results in a high machining precision (micrometer accuracy) while sparing adjacent material areas. Thermal and mechanical stresses on the non-machined areas are much lower than with other machining methods.

In the case of a further preferred version of the device according to the invention, a working beam of the beam source can be applied by the beam apparatus, in particular the deflection apparatus, in geometrically predeterminable form in a temporally predeterminable pattern to the material. Through the co-operation of the individual components, it is thus possible to produce cuts and structures. To produce a spot in which the material structure has been dissolved, a laser pulse with defined pulse parameters (pulse energy, pulse duration, focus) is generally sufficient. For cuts and structures, a large number of such spots are to be placed close alongside one another. The distance between adjacent spots should be of the order of the spot diameter at the end of the procedure. For this, the laser focus can be moved scanning over or through the material. The laser focus ideally follows a preset geometric path in 3 dimensions with micrometer precision. Thus it is possible for example to produce a cut in the material to be machined in that one desired surface after another in the tissue, for example a rectangular surface of adjacent micrometer spots, is triggered to be scanned. As a result the material cohesion is dissolved precisely in this plane and a "cut" in the tissue produced as a result. It is equally possible to apply the laser focus to the material to be machined through circular movements of the scanner in an orbit. Through a subsequent helical guiding of the working beam, a cylinder surface can thus for example be cut out of the material. As the photodisruption preferably takes place in a very narrow area, the laser beam can also act in the tissue without the material penetrated by the laser beam outside the focus being damaged. In this way, any desired geometric paths, and thus shapes, can be cut out in the material by photodisruption.

In the case of a preferred embodiment of the invention, a device is provided with which the pulsed working beam can be applied to the material by the beam-deflection apparatus and during which the repetition rate of the pulses of the working beam can be modified. By providing an apparatus for modifying the repetition rate while simultaneously guiding the beam of the working beam over the material to be machined, in this way a regular spot pattern can be elegantly produced on the material to be treated, even if the beam is directed onto the material to be machined at different angles or at different speeds by the deflection apparatus. A particularly striking advantage is achieved for example if the deflection apparatus deflects the beam in orbits onto the material to be machined and these orbits are produced with a special rotational frequency of the deflection apparatus, in particular for example the deflection mirrors. If, at a rotational frequency of for example 50 Hz, the laser beam is guided on an orbit of 1 cm diameter at a repetition rate of 300 kHz, 60,000 spots are placed uniformly distributed on each orbit per rotation. If the beam is then guided on a circle of only 0.5 cm in diameter with the same frequency of the deflection apparatus, the same distance between the individual spots on the material to be machined can be produced by reducing the repetition rate of the pulsed working beam as when guiding the beam on the larger orbit. Through a corresponding modification of the repetition rate in relation to the geometry traveled by the deflection apparatus, any desired geometric patterns can be produced on the material to be machined with an essentially constant spot distance. For example, spirals can be traveled with which, while the rotational frequency of the deflection apparatus remains constant, the repetition rate constantly decreases from the outside in. In addition, any other desired geometric shapes are conceivable. If it is not actually intended to maintain a constant distance between the individual spots on the material, but rather to achieve a higher spot density in a specific area and a lower spot density in another area, this can likewise be produced by combining the chosen parameters for the repetition rate of the working beam and the frequency or the local course of the deflection apparatus. Thus it is preferably also possible to produce gradually differing areas with a different focus density. For example, with a circle, the center can have a very low focal distance whilst the focal distance from the edge becomes ever greater.

The object is also achieved by a process for the application of fs pulses of a cavity-dumped fs oscillator beam source to a material, in particular an organic material, with which the material is machined with photodisruption or its cohesion destroyed in the focus of the laser beam.

With a particularly preferred process of the present invention, the pulsed laser beam is deflected by means of a deflection apparatus onto the material to be machined and the repetition rate of the pulses of the laser beam modified in relation to the spot pattern hereby produced on the material. In this way, any desired spot pattern and in particular any desired distance between the individual spots can be produced in the desired geometry on the material to be machined. Particularly preferably the spot patterns are distributed on the material to be machined such that the cavitation bubble of each individual spot which forms through photodisruption can be placed exactly adjacent to the cavitation bubble of the next spot. In this way, a desired cut pattern of directly adjacent cavitation bubbles then forms. For special applications, it can also be desired to place the spots even closer together. This is to be recommended for example if the material to be machined is to be replaced again after a certain period and the detachment of the material for a specific period is to be ensured before for example the drilling core or a piece otherwise cut out of the material to be machined can be removed. It is likewise conceivable that the spots are first placed at a greater distance from one another in order, in a following step, to fill the gaps between the spots and thereby form a desired pattern of cavitation bubbles.

BRIEF DESCRIPTION OF THE DRAWINGS

The device according to the invention can be used for refractive surgery by machining of the cornea or lens of the eye.

Further advantageous designs of the invention will be explained below using the drawing. There are shown in.

DETAILED DESCRIPTION

Figure 1:
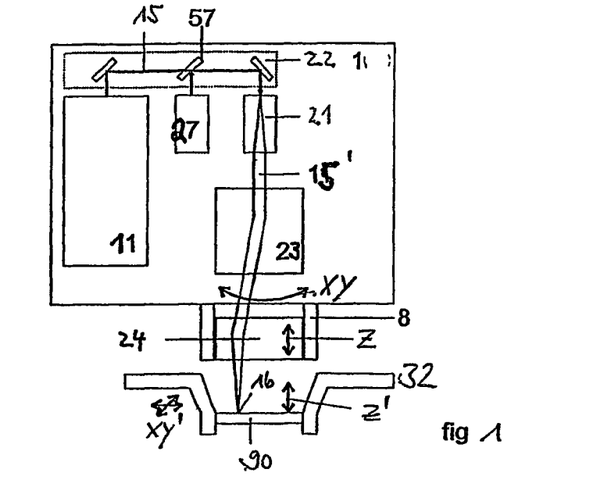
FIG. 1 a schematic representation of an embodiment of a laser according to the invention.

FIG. 1 is a schematic representation of the individual components of an embodiment of a laser system according to the invention. The machining device 1 includes a cavity-dumped fs oscillator as beam source 11. The laser beam 15 is decoupled via mirrors and a beam splitter 57 onto a beam-expansion lens system 21. The expanded laser beam 15' is then deflected in XY direction onto a beam-focusing apparatus 24 via a beam-deflection apparatus, such as for example a scanner. This is displaceable in the Z axis and thus allows the displacement of the focus point by displacement of the beam-focusing apparatus along the arrow Z. Alternatively, a focusing optical system with adjustable focal length can be used in order to displace the focus position in Z direction in controlled manner. The focused laser spot 16 is thus steered onto the material 90 to be machined which is held in position by a fixing device 32. Here, the material 90 is a contact lens to be machined. The spot 16 can also be aligned by displacing the fixing device 32 in the direction XY' or Z' on or in the material.

The laser beam 15 produced by the beam source 11 is focused on the material 90 through the machining device 1. A focus diameter of some micrometers can be achieved by focusing the laser beam 15 with a beam diameter of some millimeters through a lens system with some centimeters focal length. For example, for a Gaussian beam profile, a focus diameter of three micrometers results if a laser beam of wavelength 1000 nm and a beam diameter of 10 mm is focused with a focal length of 50 mm.

In general the laser beam 15 has at the output of the beam source 11 a smaller beam diameter than is required for optimum focusing. The beam diameter can be adapted to requirements with a beam-expansion lens system 21. A Galilean telescope set to infinity (diverging lens plus positive lens) can preferably be used as beam-expansion lens system 21. No intermediate focus results which under certain circumstances could already lead to an optical breakdown in air. Thus the remaining laser energy is greater and the beam profile constantly good. The use of lens systems which lead to optimum imaging properties of the telescope is preferred. By aligning the telescope, production variations in the beam divergence of the beam source 11 can also be compensated for.

In this embodiment the laser focus is moved scanning over or through the material. The laser focus or laser spot 16 is thus scanned in three dimensions with micrometer precision. The expanded laser beam 15' is deflected perpendicular to the original beam direction through a deflection apparatus 23. In the process, the position of the focus 16 moves according to the focusing lens system 24 perpendicular to the original beam direction. Thus the focus can be moved in a surface that is essentially flat and perpendicular to the laser beam direction (X/Y direction). The movement parallel to the beam direction (Z direction) can take place on the one hand by moving the workpiece (see arrow Z'). The scan algorithms are then preferably designed such that the workpiece need only be moved slowly and the rapid scan movements carried out by the deflection unit. On the other hand, the focusing lens system can also be moved parallel to the laser beam direction (arrow Z) in order to thus lower the focus in the Z direction. The second method is preferred, in particular in the case of medical applications, as the patient cannot generally be moved quickly enough.

The machined material 90 is fixed relative to the laser apparatus in a fixing and alignment device 32. Here, the fixing device is preferably aligned perpendicular and parallel to the beam direction in order to be able to place the cut pattern at the provided point in the material 90. A visible laser beam colinear with the machining laser beam 15, 15', from a pilot laser 27 supports the alignment.

Mirrors or mirror pairs 22 are provided for beam guidance and for fine alignment of the beam position between the individual components. The condition of the mirrors is preferably chosen such that the machining laser beam does not destroy them, the mirrors being highly reflective for the wavelength of the machining laser and sufficiently reflective for the pilot laser. The coating is preferably chosen such that the mirror does not substantially lengthen the laser pulse duration. Particularly preferably at least one of the mirrors is a so-called "chirped mirror" with which the dispersion of all the lens systems present in the beam path can be compensated to achieve optimally short pulses in the machining focus.

Figure 2:
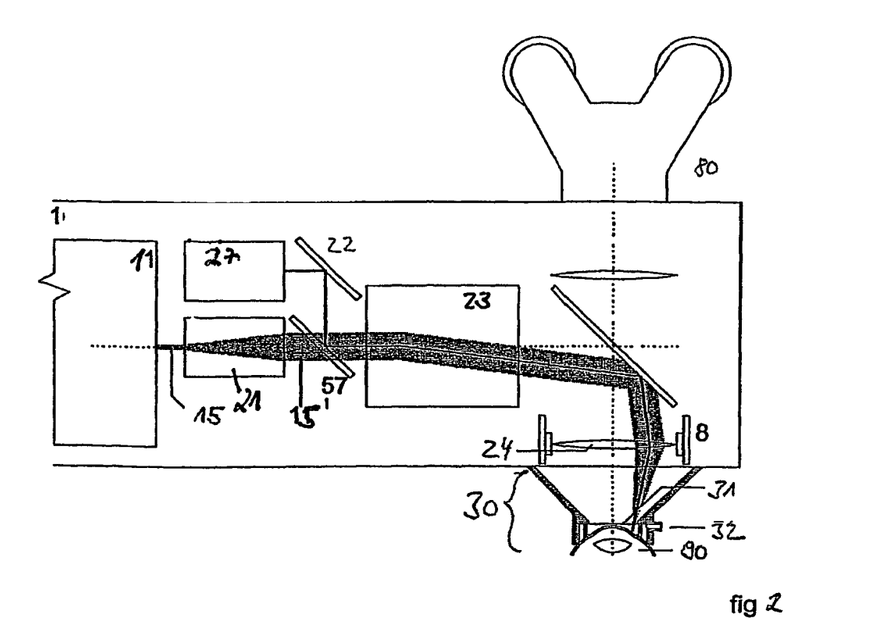
FIG. 2 a further embodiment of a laser according to the invention with surgical microscope and eye to be machined.

FIG. 2 shows a further embodiment of the present laser machining device with surgical microscope. The structure essentially corresponds to the structure in FIG. 1. Identical parts are given identical reference numbers. A human eye is provided here as material 90. By way of example, this laser apparatus with which precise cuts can be made in the cornea of the human eye will now be described in detail. A circular surface which follows the curvature of the cornea and is centered on the optical axis of the eye is cut inside the cornea with fs laser pulses. Through a circle-segment-shaped edge cut from the circular surface to the outside of the cornea a corneal flap forms which can be folded aside after the laser cut.

Such a flap serves as preparation for a LASIK operation in which the thickness of the cornea is varied by laser ablation such that refractive defects of the eye are compensated for. Currently, this cut is carried out with a mechanical keratome, which requires a great deal of practice on the part of the doctor and is risky. In addition, through a further curved circular surface which, together with the first circular surface of the flap, encloses a lenticle which can be removed after folding up the flap, a refractive correction of the cornea can take place in the same procedure.

In the particular design of the invention, the eye is pressed by a suction ring 32 onto a contact lens 31 which is either flat or preferably essentially adapted to the curvature of the cornea. The suction ring is securely connected to the beam hole of the laser apparatus, which ensures a defined position of the cornea relative to the laser focus. The expanded femtosecond laser beam is focused into the cornea with a lens system 24. A beam splitter which is highly reflective for the laser wavelength and transmitting for visible light, reflects the laser beam into the beam path of a surgical microscope which serves to observe and center the eye. The focusing lens system 24 forms part of the microscope objective. Together with a bundling lens system, a real intermediate image of the cornea can be produced which can be viewed three-dimensionally with the stereo eyepiece 80. The beam-deflection unit 23 deflects the expanded laser beam 15' perpendicular to its propagation direction. Thus the laser focus can be directed to different points in the cornea. The focus depth can be varied by moving the focusing lens system 24 along the optical axis or by adjusting the focal length of the focusing lens system.

Orbits are preferably traveled with the deflection unit. To cut the area of the circle, the radius of the circle is reduced from orbit to orbit and the repetition rate adjusted such that a uniform spot distance is retained. The focus depth is adjusted from orbit to orbit such that the cut follows the curvature of the cornea. If astigmatic corrections of the eyesight (cylinder correction) are to be introduced, the focus depth can be moved twice up and down during the orbit so that a lenticle with a cylinder lens portion forms. For the flap edge, with a fixed radius, the focus depth from the flap base is slowly moved to the outside of the cornea so that a cylinder casing is produced. On an arc section of the circles described, the laser beam must be interrupted in order to leave a "hook" on which the prepared flap is securely held. For this, the decoupling of laser pulses from the beam source 11 is simply interrupted.

The beam source 11 is a "cavity-dumped" femtosecond oscillator which is preferably directly diode-pumped and thus simple and reliable. The emitted laser beam 15 is preferably expanded to 1-2 cm beam diameter with a Galilean telescope. Colinear to the expanded laser beam 15' a visible laser beam is superimposed from a pilot laser 27, and is then scanned and focused together with the machining laser beam. For this purpose, the beam splitter 57 is transparent for the femtosecond laser wavelength and reflective for the pilot beam.

The variety of possible cut figures depends only on the scan algorithms. In principle a laser apparatus as described is suitable for a large number of applications (for example for refractive corrections of eyesight) in which cuts or structural transformations are to be undertaken within the transparent constituents of the eye (cornea, lens, vitreous body) and on the non-transparent parts such as sclera, iris, ciliary body. The invention is thus far superior to existing technologies in terms of universality and precision even in this small partial field of use (sparing surrounding tissue).

Figure 3:
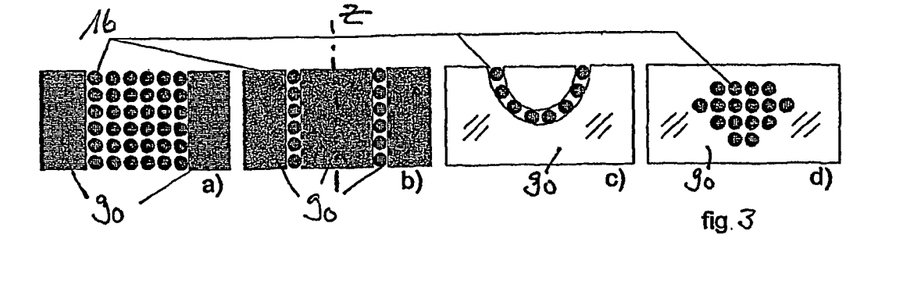
FIG. 3 a schematic representation of some examples of possible cut patterns that can be carried out with the laser system according to the invention.

FIG. 3 shows in the detail views 3a to d application examples of cut geometries which can be realized with the laser system according to the invention. These uses are examples only—any other desired geometries can be realized. The cohesion of the material 90 is destroyed in the focus 16 of the laser (photodisruption). In general this is accompanied by a local evaporation of the material. Following the action of the laser pulse, the material structure is destroyed permanently, or for a period lasting at least to the end of the machining period, in a small volume, the cavitation bubble (hereafter also called spot 16). The use of a hard-focused femtosecond laser or oscillator thus offers the most precise localization of the laser action. In the sharply delimited focus area, the material structure is thus destroyed whereas in closely adjacent areas (even less than a micrometer away) in general no change in the material takes place. This results in a high machining precision while sparing adjacent material areas.

For cuts and structurings, a large number of individual spots which break up the material structure are placed closely alongside one another. The distance between adjacent spots should be of the order of the spot diameter at the end of the procedure. In FIG. 3a, a predetermined volume (e.g. a bore in the material) is generated by completely filling the volume to be ablated with individual spots 16. In the case of such a non-transparent material, the procedure is carried out in layers beginning with the layer of spots facing the laser.

In FIG. 3b, the edge of the bore is covered with spots. Here a cut through the material is to be shown. The spots 16 are to be arranged rotation-symmetrical about the axis Z drawn in broken lines. In this way, a drilling core is produced in the middle of the machined material 90. The drilling core can then be removed as a cohesive piece. The required number of laser pulses thus falls substantially, in particular with large cross-sectional surface areas of the bore, compared with FIG. 3a.

FIG. 3c shows an undercut in a transparent material 90. As the radiation from the material 90 is not absorbed, coherent material pieces can be removed from the material by placing spots on the cut edge if it borders the surface.

FIG. 3d shows how cavities or structures (e.g. changes in the optical properties) can be produced in a transparent material, depending on the composition of the material.

For macroscopic cut figures (in the centimeter range) some millions of laser spots are required even to cover only the cut surface (as in FIGS. 3b and c) densely enough with spots. For many applications (in particular medical applications) it is advantageous to keep the machining or treatment time as short as possible. The beam source of the laser apparatus should therefore be capable of emitting laser pulses at a high repetition rate. Femtosecond laser oscillators operating continuously (in cw-mode-locking operation) according to the state of the art mostly have repetition rates of some tens of MHz—the pulse energies in the nJ range are not sufficient, in the case of sufficiently large focal lengths of the focusing lens system (working distance of some cm), to produce an optical breakdown in the material. This is achieved, however, with a laser system according to the invention.

Figure 4:
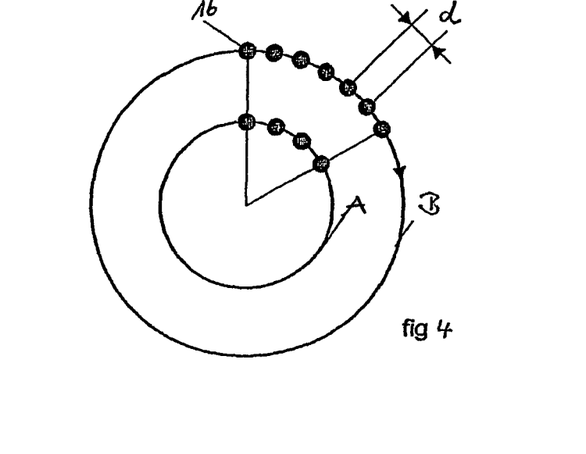
FIG. 4 a schematic detailed view of a sequence of laser spots on circular lines.
Figure 5:
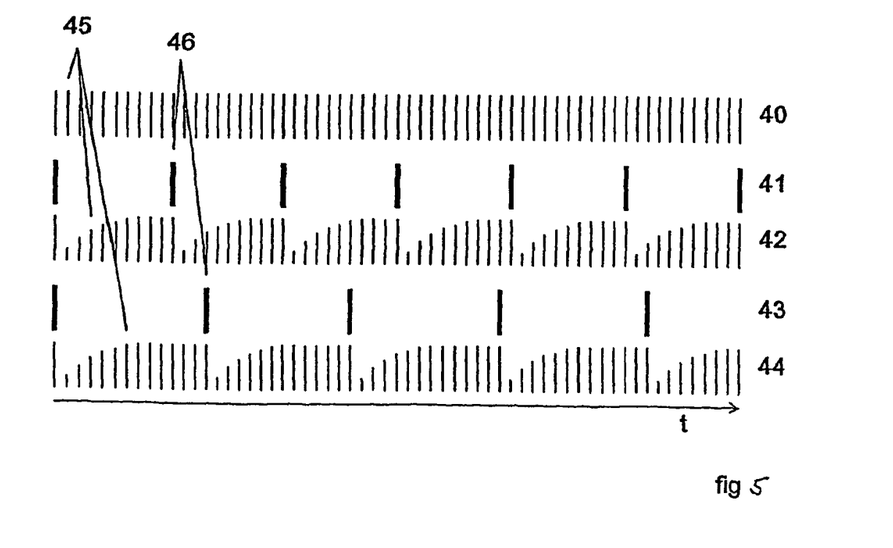
FIG. 5 the chronological pattern of sequences of laser pulses in and outside of the laser resonator.

FIG. 4 shows schematically a section from a possible scan pattern in which the individual spots 16 machined by individual laser pulses are arranged along paths which can be traveled continuously by the scanner. In order to achieve a sufficiently large spot distance at high repetition rates of the beam source 11, the focus is moved very rapidly in at least one of three scan dimensions. The scan algorithms are therefore preferably such that the spots are placed along paths which correspond to the natural movements of the deflection unit. The movement in the other two dimensions can then take place relatively slowly. The natural paths of the deflection unit can be e.g. orbits which can travel the deflection units at fixed rotation frequencies. This can take place e.g. by rotating optical elements in the deflection unit. The radius of the orbit and the focus depth (Z direction) are then the scan variables that can be changed slowly. This variant is particularly suitable if rotation-symmetrical cut figures have to be produced. The repetition rate of the laser can be particularly effectively used when the rotation frequency of the orbits is chosen such that, in the case of the largest orbits (B) to be traveled, the full repetition rate of the beam source leads to the desired spot distance d. If the radius (A) of the orbits becomes smaller upon traveling the cut pattern, the repetition rate of the source can be reduced correspondingly with the result that the optimum spot distance again results. This adjustment of the repetition rate is directly possible with a suitable cavity-dumped oscillator. An adjustment of the rotation frequency to the repetition rate of the source can be more difficult technically, in particular if this is continuous for each orbit (A, B). To reduce the machining time, however, an adjustment of the rotation frequency in a few steps to the smaller orbits can be advantageous. FIG. 5 shows possible sequences of laser pulses in and outside of the laser resonator. The rotation frequency of the laser pulses in the oscillator 40 depends only on the resonator length and is preset for a specific beam source, and is about 100 MHz with resonator lengths of some meters. The principle of cavity dumping is to decouple a portion of the pulse 45 rotating in the resonator with a switchable optical element at a specific time. A large proportion of the intracavity pulse energy leaves the beam source and is conducted as an output laser pulse 46 into the beam-deflection system.

The pulse energy remaining in the resonator is reamplified to its saturation value 42 after a number of rotations in the resonator and can then be decoupled anew. The decoupled laser pulses 46 thus have a lower repetition rate than the intracavity pulses 45. The maximum repetition rate is preset by the time until the saturation pulse energy is regained after decoupling of a laser pulse. The pattern of the intracavity pulse energy then approximately corresponds to the behavior shown as 42 in FIG. 5.

The repetition rate can easily be reduced by decoupling 43, 44 again only a certain time after the saturation pulse energy is reached. The time between two decoupled laser pulses (reciprocal of the repetition rate) can therefore be set freely between infinite (repetition rate zero) and a minimum (maximum repetition rate) in steps of the resonator rotation time. Thus the pulse sequence frequency can be adapted to the deflection speed of the beam-deflection system. At typical ratios of the decoupled repetition rate to the rotation frequency in the resonator of 1:100-1:1000, the number of laser spots placed per rotation of the deflection unit can thus be varied in minimum steps of 0.1-1%. The spot distances on different orbits then scatter only by fractions of one percent.

With the present invention, a laser apparatus has been provided which comprises a femtosecond beam source and preferably also means for beam formation and guidance, a programmable beam deflection, a beam focusing and a device for positioning and fixing the material or tissue to be machined. The device is preferably suitable for precise cutting and structuring in respect of laser pulse parameters, repetition rate and deflection speed and accuracy. In the case of materials transparent for the laser wavelength, the machining can also take place inside the material. The material to be removed need not be ablated completely by the laser, coherent material areas can rather be removed intact through suitable cut control. The cutting accuracy depends on the diameter of the laser focus and lies in the micrometer and submicrometer ranges. The use of laser pulses with a pulse duration clearly below a picosecond reduces the collateral material or tissue damage almost completely and thus substantially contributes to machining precision and allows in particular the medical treatment of sensitive tissues in vivo.

The invention claimed is:

1. A device for precise machining of a material, comprising:
   a pulsed laser system having a beam source including a cavity-dumped femtosecond oscillator, the beam source being configured to generate radiation having a pulse energy in a range from 100 nJ to 10 μJ and a pulse duration in a range from 100 femtoseconds to 1 picosecond; and
   a holding device configured to fix the material in a defined position relative to the beam source such that an output of the cavity-dumped femtosecond oscillator is directed to the material so as to destroy a cohesion of the material using photodisruption.

2. The device as recited in claim 1, wherein the material is an organic material.

3. The device as recited in claim 1, further comprising a beam apparatus for at least one of a beam formation, a beam guidance, a beam deflection and a beam focusing.

4. The device as recited in claim 3, wherein the beam apparatus is programmable.

5. The device as recited in claim 3, wherein the beam apparatus is configured to apply a working beam of the beam source to the material in a geometrically predeterminable tbrm and in a temporally predeterminable pattern.

6. The device as recited in claim 5, wherein the beam apparatus includes a beam deflection device and wherein a repetition rate of the working beam is changeable during application of the working beam to the material.

7. The device as recited in claim 1, wherein the pulse energy is 1 µJ.

8. The device as recited in claim 1, wherein the cavity dumped femtosecond oscillator is configured to provide laser pulses with repetition rates from 10 kHz to 10 MHz.

9. The device as recited in claim 1, wherein the material includes an eye of a human patient.

10. The device as recited in claim 1, wherein the material includes a cornea of a human patient.

11. The device as recited in claim 1, wherein the beam source is configured to generate radiation having a pulse energy in a range from 500 nJ to 5 µJ.

12. The device as recited in claim 1, wherein the beam source is configured to generate radiation having a pulse duration in a range from 200 femtoseconds to 300 femtoseconds.

13. A method for applying a laser beam to a material, the method comprising:

provided a laser beam having femtosecond pulses using a beam source including a cavity-dumped femtosecond oscillator, the pulses having an energy in a range from 100 nJ to 10 µJ;

directing the laser beam on the material so as to destroy a cohesion of the material in a focus of the laser beam using photodisruption.

14. The method as recited in claim 13, wherein the material is an organic material.

15. The method as recited in claim 14, further comprising performing refractive surgery using the laser beam.

16. The method as recited in claim 13, further comprising guiding the pulsed laser beam onto the material using a deflection apparatus and modifying a repetition rate of the femtosecond pulses in relation to a spot pattern produced on the material.

17. The method as recited in claim 13, wherein the material includes an eye of a human patient.

18. The method as recited in claim 13, wherein the material includes a cornea of a human patient.

19. The method as recited in claim 13, wherein the pulses have an enemy in a range from 500 nJ to 5 µJ.

* * * * *